United States Patent [19]

Bigazzi

[11] 4,267,101

[45] May 12, 1981

[54] PROCESS FOR OBTAINING HUMAN RELAXIN FROM FETAL MEMBRANES

[75] Inventor: Mario Bigazzi, Florence, Italy

[73] Assignee: Serono Laboratories Inc., Braintree, Mass.

[21] Appl. No.: 117,444

[22] Filed: Feb. 1, 1980

[51] Int. Cl.³ .................. A61K 35/48; A61K 35/54
[52] U.S. Cl. .......................... 260/112 R; 260/112 B; 424/97; 424/177; 435/68
[58] Field of Search ................ 260/112 B, 112 R; 424/97, 177; 435/68

[56] References Cited

U.S. PATENT DOCUMENTS

| | | | |
|---|---|---|---|
| 2,852,432 | 9/1958 | Phillips | 424/97 |
| 2,930,737 | 3/1960 | Cohen | 424/97 |
| 2,995,494 | 8/1961 | Singher et al. | 424/97 |

OTHER PUBLICATIONS

Chem. Abstracts, vol. 89, 1978, 212863w, Weiss et al.
Biochem. Biophys. Res. Commun. 1975, 68(4), 1126–1321, Schwabe et al.

*Primary Examiner*—Howard E. Schain
*Attorney, Agent, or Firm*—Ostrolenk, Faber, Gerb & Soffen

[57] ABSTRACT

Human Relaxin is recovered from human fetal membranes, and preferably from the chorion-decidua membranes.

6 Claims, No Drawings

PROCESS FOR OBTAINING HUMAN RELAXIN FROM FETAL MEMBRANES

Relaxin is a polypeptide hormone that facilitates relaxation of the pelvic ligament of mammals. Hisaw (Proc. Soc.Exp.Biol. 23,661,1926) first observed the existence of Relaxin in 1926. Despite the numerous years that have passed since its first discovery, little information about this hormone is available, especially in the humans.

In animals, Relaxin has been found in various tissues of mammals and non-mammals. So far, the only rich and abundant source of Relaxin is the ovary of the pregnant sow, from which Relaxin is obtained for commercial and experimental use.

In humans, very little is known about the origin, the physiological or pathological role, and the structure of Relaxin.

The pregnant ovary seems to be rich in Relaxin-like activity also in the woman. However, the possibility to obtain human Relaxin from this source is very poor due to the practical impossibility of having sufficient amounts of human pregnant ovaries available for the extraction procedure.

This invention is based on the discovery that a new, easily available source of human Relaxin is the complex of fetal membranes that are easily obtained at delivery together with placenta.

More specifically, it has been found that the decidual membrane is particularly rich in Relaxin.

The so-called "fetal membranes" are a complex of the three layers amnion, chorion and decidua.

Amnion is easily separated from the associated chorion-decidua membranes through delamination. On the contrary, chorion and decidua are difficult to be separated completely from each other.

The main object of this invention is a process for obtaining Relaxin which uses the fetal membranes as the source material. Preferably, the associated chorion-decidua membranes or, more preferably, the decidua itself is used as such source material.

Human Relaxin can be obtained directly from the above source(s) by extraction or, indirectly, from the incubation medium of in vitro cultures of the said tissue(s) or cells.

Bioassay of Relaxin containing preparations is generally based on the following methods:
(1) the inhibition of spontaneous uterus contraction both in vivo and in vitro; and
(2) the relaxation of the symphis pubis which can be determined by:
  (a) palpation of the guinea pig symphis pubis;
  (b) X-ray of mouse symphis pubis; or
  (c) direct measurement of mouse symphis pubis.

The biological activity of the Relaxin containing preparations obtained in accordance with this invention has been measured following method 2c above and expressed in GPU (guinea pig units) in accordance with the porcine Relaxin preparation used as standard (NIH).

The preparations of the invention were also found to be active in the uterus contraction inhibition test (see 1 above).

Relaxin can be used therapeutically in various pathologic conditions of pregnancy (precocious delivery, threatened abortion) and of connective tissue (sclerodermia and trofic ulcer). Furthermore, human Relaxin is of utmost importance in the preparation of a homologous radioimmunoassay kit allowing the measurement of Relaxin in human body fluids and tissues.

The following non limitative examples illustrate the invention.

EXAMPLE 1

Human Relaxin from Tissue Homogenate

Human placenta and the associated fetal membranes are collected at delivery and washed in Hank's solution or buffered saline, ph 7.4. The material is stored at $-30°$ C. until processed (Placenta can be separated from the association fetal membranes either before or after storage).

The fetal membranes as a whole can then be processed or, preferably, amnion is separated from the decidua-chorion membranes by delamination and discarded. If desired, decidua can be scraped from chorion and processed as such. However, the latter operation is not performed easily and does not appear to be worthy for routinary extraction procedures.

Approximately 500 gr of membrane material coming from 15 to 20 deliveries are processed at one time. The tissue is minced and homogenized in 200 ml distilled water. The so-obtained tissue homogenate is then processed according to either of the following methods:
(a) according to Schwabe and Braddon, Biochem. Biophys. Res. Commun. 68,1126,1976: after addition of 30 ml concentrated HCl, the mixture is kept at 4° C. for 24 hours, then 160 ml of cold acetone are added and the mixture is kept overnight at 4° C. The precipitate is separated by centrifugation at 2000 rpm for 15 min and discarded. The clear supernatant is treated with 5 volumes of cold acetone for 24 hours and then centrifuged at 27,000 rpm for 30 min.
(b) according to Sherwood, Endocrinology 104,886,1979: the mixture is first extracted with phosphate buffer, then the tissue residues and the heaviest cellular organelles are separated by centrifugation at 27,000 rpm for 30 min and discarded.

In both cases, Relaxin as a crude extract is obtained. The crude extract can be further purified by serial chromatography on CM-cellulose, Sephadex G-50 superfine and Sephadex G-15 following the methods proposed by the said Authors to give a purified material having total Relaxin activity of 1500 to 2500 GPU and specific activity from 150 to 1500 GPU/mg proteins depending on the number of the chromatographic steps.

EXAMPLE 2

Human Relaxin from in Vitro Culture of Human Decidua

Decidua is scraped from the surface of the decidua-chorion associated membranes and minced.

1 to 2 grams of the minced tissue are placed in Erlenmeyer flasks filled each with 40 ml of oxygenated Gey's solution modified by the addition of Hepes (20 mM), Penicilline (50 U/ml) and 10% calf serum.

The cultures are incubated in a metabolic incubator for 48 hours at 37° C. The media are collected, treated with 5 volumes of cold acetone and kept at 4° C. for 24 hours. The mixture is then centrifuged at 27,000 rpm for 30 min to give a pellet containing a crude Relaxin extract with a specific activity of 500 to 2000 GPU/mg proteins.

The crude extract can then be further purified, according to the known methods referred to in Example 1.

I claim:

1. A process for obtaining human Relaxin which comprises the steps of:
   (a) mincing and homogenizing human fetal membranes; and
   (b) precipitating and discarding the tissue residues and the heaviest cellular organelles to obtain a crude Relaxin extract.

2. A process according to claim 1 wherein amnion is separated from the associated chorion-decidua membranes and discarded, the chorion-decidua membranes being used as the source material in step (a).

3. A process according to claim 1 or 2 wherein decidua is scraped from the associated chorion membrane and used as the source material in step (a).

4. A method of producing human Relaxin by in vitro culture which comprises the steps of:
   (a) incubating human decidual tissue or cells; and
   (b) purifying Relaxin from the incubation medium by conventional procedures.

5. In a process of obtaining human Relaxin by recovery from human source material, the improvment which comprises employing fetal membranes as said source material.

6. The process of claim 5 wherein said fetal membrane is chorion-decidua membranes.

* * * * *